United States Patent [19]

Pilgram

[11] 4,345,077
[45] Aug. 17, 1982

[54] CERTAIN HERBICIDAL N-(META-(6-CHLORO-3-PYRIDAZINYLOXY)PHENYL)TRIFLUOROMETHANESULFONAMIDES

[75] Inventor: Kurt H. Pilgram, Modesto, Calif.

[73] Assignee: Shell Oil Company, Houston, Tex.

[21] Appl. No.: 118,354

[22] Filed: Feb. 4, 1980

[51] Int. Cl.$^3$ ............................................. C07D 237/14
[52] U.S. Cl. .......................................... 544/241; 71/92
[58] Field of Search ........................................... 544/241

[56] References Cited

U.S. PATENT DOCUMENTS

| | | | |
|---|---|---|---|
| 3,652,257 | 3/1972 | Jojima | 544/241 |
| 3,686,192 | 8/1972 | Moore | 546/293 |
| 3,840,597 | 10/1974 | Moore | 544/107 |
| 3,906,024 | 9/1975 | Moore | 260/465 E |

OTHER PUBLICATIONS

Moore et al. IV, Chem. Abs. 78, 43073d (1972).

Primary Examiner—Mark L. Berch

[57] ABSTRACT

Certain N-(meta-(6-chloro-3-pyridazinyloxy)phenyl)trifluoromethanesulfonamides and their use as herbicides.

2 Claims, No Drawings

CERTAIN HERBICIDAL N-(META-(6-CHLORO-3-PYRIDAZINYLOXY)-PHENYL)TRIFLUOROMETHANESULFONA-MIDES

DESCRIPTION OF THE INVENTION

It has been found that useful herbicidal properties are possessed by certain sulfonamides of the formula

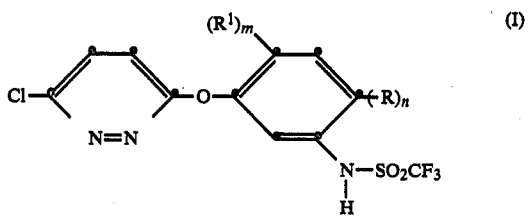

wherein m and n each is zero or one, R is nitro, methyl, chlorine or fluorine, and $R^1$ is methyl, chlorine or fluorine.

Typical, exemplary individual species of the class of compounds, the manner in which they can be prepared and isolated, and summaries of their herbicidal testing, are set forth in the Examples hereinafter. Other typical individual species of the class are the following (in which the symbols refer to Formula I):

| n | R | m | $R^1$ |
|---|---|---|---|
| 1 | Cl | 0 | — |
| 0 | — | 1 | Cl |
| 1 | F | 1 | F |
| 1 | Cl | 1 | —CH3 |
| 1 | —CH3 | 1 | Cl |

The compounds of Formula I can be prepared by the following general sequence of reactions:

(a) treating a mixture of 3,6-dichloropyridazine and the appropriate meta-aminophenol,

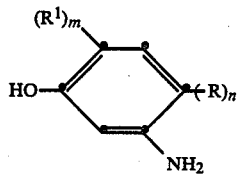

wherein R is other than nitro, in a solvent, such as dimethyl sulfoxide, with a strong base, such as a concentrated aqueous solution of sodium hydroxide, or sodium hydride, to form the corresponding 3-(6-chloro-3-pyridazinyloxy)benzeneamine;

(b) treating a chilled solution of the amine in a solvent such as methylene chloride, with trifluoromethanesulfonic anhydride in the presence of, or then adding, a nitrogen base, such as triethylamine.

Species wherein R is nitro can be prepared by nitrating the product of step (b), as by adding the product (b) to concentrated nitric acid at a low temperature—i.e., about 0°-5° C.

Some of the amino phenol precursors are known compounds; the others can be prepared by known methods.

Preparation of typical individual species of the compounds of Formula I is described in the following examples. In each case, the identities of the products and of intermediates involved were confirmed by appropriate chemical and spectral analyses.

EXAMPLE 1

N-(3-(6-chloro-3-pyridazinyloxy)phenyl)-1,1,1-trifluoromethanesulfonamide (1)

A concentrated aqueous solution of 44 g of sodium hydroxide was added to a stirred solution of 149 g of 3,6-dichloropyridazine and 114.5 g of meta-aminophenol in 500 ml of dimethyl sulfoxide, at room temperature. The stirred mixture was heated, refluxed (150°-155° C.) for two hours, cooled, and filtered. The filter cake was recrystallized from aqueous methanol to give 3-(6-chloro-3-pyridazinyloxy)benzeneamine (1A), as an off-white solid, mp: 76°-77° C.

28.2 g of trifluoromethanesulfonic anhydride was added drop-by-drop over a ten-minute period to a chilled (−20° C.) and stirred solution of 22.1 g of 1A in 200 ml of methylene chloride. The resulting mixture was allowed to stand at room temperature for 18 hours, and the volatile materials therein were evaporated under reduced pressure. The residue was dissolved in 100 ml of tetrahydrofuran. The solution was poured into 300 ml of ice water, neutralized with 8.4 g of sodium bicarbonate and extracted with ether. The extract was washed with water, and dried over anhydrous magnesium sulfate, and the solvent was evaporated. The residue was recrystallized from 1/1 (v/v) ether/hexane to give 1, as a tan solid, mp: 165°-165° C.

EXAMPLE 2

N-(5-(6-chloro-3-pyridazinyloxy)-2-nitrophenyl)-1,1,1-trifluoromethanesulfonamide (2)

15 g of 1 was added in portions to 200 ml of chilled (4°-5° C.), stirred 90% nitric acid, and the mixture was stirred at 4° C. for 30 minutes. The resulting mixture was poured into ice water and the resulting solid was filtered. The filter cake was washed with water and purified by silica gel column chromatography, using as eluent a 66:30:4 (v:v:v) mixture of hexane, ethyl acetate and tetrahydrofuran, to give 2, as an amber glassy solid.

EXAMPLE 3

N-(5-(6-chloro-3-pyridazinyloxy)-2-methylphenyl)-1,1,1-trifluoromethanesulfonamide (3)

70 g of 3-nitro-4-methylphenol, prepared according to German Offenlegungschrift No. 2,213,568, 200 ml of tetrahydrofuran and 2 g of activated Raney nickel catalyst were placed in a Parr bomb. The mixture was shaken for 3.5 hours under 60 p.s.i. hydrogen pressure. The mixture then was filtered and the solvent was evaporated from the filtrate. The residue was recrystallized from ether to give 3-amino-4-methylphenol (3A), as a grey solid, mp: 145°-148° C.

14.9 g of 50% sodium hydride in mineral oil freshly washed with hexane was added in portions over a 15-minute period to a stirred mixture of 46.7 g of 3,6-dichloropyridazine, 38.3 g of 3A and 250 ml of dimethyl sulfoxide, the temperature being held below about 40° C. The mixture was allowed to stand at room temperature for 18 hours, then was poured over ice water and extracted with methylene chloride. The extract was washed with ice water and dried (magnesium sulfate), and the volatile materials were evaporated. The residue was chromatographed over silica gel, using the eluent described in Example 2, to give 5-(6-chloro-3-pyridazinyloxy)-2-methylbenzeneamine (3B), as a tan solid, mp: 83°-85° C.

20 g of trifluoromethanesulfonic anhydride was added drop-by-drop to a stirred mixture of 16.0 g of 3B and 200 ml of methylene chloride at 0° C. Then 6.9 g of triethylamine was added, drop-by-drop, to the stirred mixture, at 0° C. The stirred mixture then was allowed to warm to room temperature and stirred for one hour. The mixture was poured over ice water and the organic phase was dried (magnesium sulfate) and the solvent was evaporated from the filtrate, to give 3, as an amber syrup.

EXAMPLES 4 and 5

By the method described in Example 4, there were prepared the individual species wherein (referring to Formula I):

Example 4 (Compound 4): m and n each is 1, R and $R^1$ each is —$CH_3$, as a brown solid, mp: 177°-180° C.

Example 5 (Compound 5): m and n each is 1, R and $R^1$ each is Cl, as a colorless solid, mp: 204°-206° C.

Compounds of Formula I have been found to be useful for killing unwanted plants, being active with respect to both broad-leaved plants and grasses, and being effective when applied either preemergence (applied to the soil before the plants have sprouted) or postemergence (to the foliage of the growing plants).

Accordingly, the invention includes a method of killing unwanted plants which comprises applying to the locus an effective amount of a compound of Formula I. Likewise the invention also includes herbicidal compositions comprising a carrier or a surface-active agent, or both a carrier and a surface-active agent, and, as active ingredient at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, nonsedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

Protection of a locus or area from undesirable plants is effected by applying a compound of Formula I, ordinarily in a composition of one of the aforementioned types, to the foliage of the plants or plant growth medium, e.g., soil in which the plant is growing or in which the seeds are present. The active compound, of course, is applied in an amount sufficient to exert the desired action.

The amount of compound of the invention to be used in controlling undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound of Formula I will be satisfactory.

EXAMPLES OF HERBICIDAL ACTIVITY

The preemergence herbicidal activity of the compounds of the invention was evaluated by planting seeds of watergrass (*Echinochloa crus-galli*), garden cress (*Lepidium sativum*), downy brome (*Bromus tectorum*), velvetleaf (*Abutilon theophrasti*), yellow foxtail (*Setaria lutescens*), and sicklepod (*Cassia obtusifolia*) in test tubes, nominally measuring 25×200 millimeters, filled about three-quarters full of untreated soil, in each case covered on top with about 2.5 cubic centimeters of soil treated with the test compound at the rate of 0.1 and 1 milligram per tube designated in Table I at Rates I and II, respectively. The dosages of test compound were approximately two and twenty pounds of test compound per acre, respectively. The seeds were planted in the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Living tissue, but plant expected to die |
| 7 | Plant badly damaged, but expected to live |
| 6 | Plant badly damaged, but expected to recover completely |
| 5 | Unacceptable damage for crop plants, insufficient damage to weeds |
| 3–4 | Definite damage |
| 1–2 | Plant slightly affected, possible by the chemical, possibly due to biological variability |
| 0 | No visible effect |

The postemergence activity of the compounds of this invention was evaluated by spraying 10-day old large crabgrass (*Digitaria sanguinalis*) plants, 13-day old redroot pigweed (*Amaranthus retroflexus*) plants, 6-day old Johnsongrass (*Sorghum halopense*) plants, 9-day old velvetleaf plants, 9-day old yellow foxtail plants and 9-day old sicklepod plants to runoff with a liquid formulation of the test compound at the rates of 2.4 milliliters of a 0.025% solution (about one pound of Compound I per acre), designated Rate I in Table I, and 2.4 milliliters of a 0.25% solution (about ten pounds of Compound I per acre), designated Rate II in Table I. The sprayed plants were held under controlled conditions of temperature, moisture and light for 7 to 8 days and the effect of Compound I was then evaluated visually, the results being rated on the 0 to 9 scale described above.

The results of the tests are summarized in Table I.

TABLE I
HERBICIDE SCREEN RESULTS

| | Dosage | | | | | | | | | | | | | | | | | | | | | | | |
|---|---|---|---|---|---|---|---|---|---|---|---|---|---|---|---|---|---|---|---|---|---|---|---|---|
| | Preemergence (Soil) | | | | | | | | | | | | Postemergence (Foliar) | | | | | | | | | | | |
| | Watergrass | | Garden Cress | | Downy Brome | | Velvetleaf | | Yellow Foxtail | | Sicklepod | | Crabgrass | | Pigweed | | Johnsongrass | | Velvetleaf | | Yellow Foxtail | | Sicklepod | |
| | I | II | I | II | I | II | I | II | I | II | I | II | I | II | I | II | I | II | I | II | I | II | I | II |
| 1 | 8 | 9 | 8 | 9 | 9 | 9 | 8 | 8 | 7 | 8 | 2 | 7 | 5 | 8 | 7 | 9 | 7 | 7 | 7 | 8 | 7 | 8 | 7 | 8 |
| 2 | 8 | 8 | 8 | 8 | 8 | 9 | 7 | 8 | 8 | 8 | 7 | 8 | 2 | 7 | 6 | 8 | 8 | 8 | 7 | 8 | 7 | 8 | 8 | 8 |
| 3 | 7 | 8 | 9 | 9 | 8 | 9 | 7 | 9 | 5 | 8 | 5 | 7 | 1 | 2 | 2 | 8 | 2 | 6 | 7 | 8 | 6 | 8 | 7 | 8 |
| 4 | 7 | 8 | 8 | 9 | 5 | 9 | 6 | 7 | 7 | 9 | 0 | 7 | 5 | 5 | 5 | 9 | ,0 | 4 | 7 | 8 | 3 | 6 | 6 | 7 |
| 5 | 8 | 9 | 8 | 9 | 9 | 9 | 7 | 9 | 7 | 9 | 7 | 9 | 5 | 4 | 8 | 8 | 7 | 9 | 6 | 9 | 6 | 8 | 7 | 8 |

I claim:

1. A compound of the formula

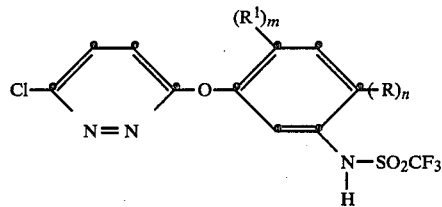

wherein m and n each is zero or one, R is nitro, methyl, chlorine or fluorine, and $R^1$ is methyl, chlorine or fluorine.

2. A compound according to claim 1 wherein m is zero and n is one, and R is chlorine or methyl.

* * * * *